(12) United States Patent
Diekmann

(10) Patent No.: US 6,392,234 B2
(45) Date of Patent: *May 21, 2002

(54) INFRARED OPTICAL GAS SENSOR

(75) Inventor: Wilfried Diekmann, Lübeck (DE)

(73) Assignee: Drager Sicherheitstechnik GmbH (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/314,406

(22) Filed: May 19, 1999

(30) Foreign Application Priority Data

Aug. 5, 1998 (DE) .......................................... 198 35 335

(51) Int. Cl.$^7$ .................................................. G01J 5/10
(52) U.S. Cl. .............................. 250/338.3; 250/339.01; 250/344; 250/343
(58) Field of Search .................... 250/338.3, 339.01, 250/339.02, 344, 343, 349; 257/440

(56) References Cited

U.S. PATENT DOCUMENTS

| | | | | |
|---|---|---|---|---|
| 2,898,800 A | * | 8/1959 | Bergson | 356/406 |
| 3,962,578 A | * | 6/1976 | Roschen | 250/226 |
| 4,650,833 A | * | 3/1987 | Sakagami et al. | 525/356 |
| 4,692,622 A | | 9/1987 | Taniguchi et al. | |
| 4,803,360 A | * | 2/1989 | Ball et al. | 250/338.3 |
| 4,806,763 A | * | 2/1989 | Turnball | 250/338.3 |
| 5,055,688 A | | 10/1991 | Fabinski | |
| 5,124,553 A | * | 6/1992 | Hilliard et al. | 250/344 |
| 5,311,019 A | * | 5/1994 | Gammarino | 250/338.3 |
| 5,455,421 A | * | 10/1995 | Spears | 250/384 |
| 5,631,460 A | * | 5/1997 | Gray et al. | 250/226 |
| 5,808,350 A | * | 9/1998 | Jack et al. | 257/440 |
| 5,908,789 A | * | 6/1999 | Weckström | 436/133 |

FOREIGN PATENT DOCUMENTS

| | | |
|---|---|---|
| DE | 197 12 823 A1 | 10/1997 |
| DE | 197 13 928 C1 | 4/1998 |
| EP | 0 427 037 A2 | 5/1991 |
| EP | 0 799 650 A2 | 10/1997 |
| GB | 834437 | 5/1960 |
| GB | 2 245 705 A | 1/1992 |

* cited by examiner

*Primary Examiner*—Constantine Hannaher
*Assistant Examiner*—Albert Gagliardi
(74) *Attorney, Agent, or Firm*—McGlew & Tuttle, P.C

(57) ABSTRACT

An infrared optical gas sensor is improved with respect to the quality of the measured signal. The infrared radiation detectors (4, 6) used as the reference radiation and measuring radiation detectors include thin layers of a partially transparent material, which sends an electric measured signal that depends on the radiation intensity received. The infrared radiation detectors are arranged stacked one over the other and with an interposed narrow-band filter (3, 5) each, which are transparent at the measuring wavelength. The infrared radiation detectors have an electrically conductive coating on the top side and the underside and are contacted. The measuring radiation detector (6) follows the reference radiation detector (4) in the direction of the beam and the reference radiation detector (4) is transparent for at least part of the measuring radiation at the measuring wavelength, or the reference radiation detector follows the measuring radiation detector in the direction of the beam, and the measuring radiation detector is transparent for at least part of the reference radiation at the reference wavelength.

20 Claims, 3 Drawing Sheets

INFRARED OPTICAL GAS SENSOR

FIELD OF THE INVENTION

The present invention pertains to an infrared optical gas sensor with at least one infrared radiation source and with at least one infrared radiation detector.

BACKGROUND OF THE INVENTION

Such an infrared optical gas sensor is disclosed, e.g., in DE 197 13 928 C1 and it contains especially two radiation sources and two radiation detectors as well as associated optical concentrators and a beam splitter.

An essential drawback of the infrared optical gas sensors used hitherto is due to the relatively complex optical design and the cost of the optical components that is associated with it, because two wavelengths, namely, a measuring wavelength and a reference wavelength, are usually used to compensate the effect of the reduction of the radiation intensity of the infrared radiation source due to its aging or due to the contamination of optical surfaces in the beam path. The measuring wavelength (measuring radiation) is selected to be such that the corresponding measured signal of an infrared radiation detector displays a characteristic dependence on the concentration of the gas to be measured. On the other hand, the reference wavelength (reference radiation) is selected to be such that the reference signal measured is affected by the gas to be measured as little as possible. The geometric design of the measuring and reference channels is selected to be such that the radiation will possibly take the same optical path in the measuring and absorption sections for both channels.

The radiation is divided between two separate optical paths for the measuring radiation and the reference radiation in a usually encapsulated area not affected by the gas to be measured, especially by means of a beam splitter. The effect of the above-mentioned changes in the radiation intensity, which affect both channels, is to be eliminated by dividing the signal values of the measuring channel and the reference channel, while the change in the measured signal of the narrow spectral band absorption by the measured gas is preserved.

These hitherto usual measuring arrangements and the corresponding measurement methods have the fundamental drawback that a change in the geometry of the beam distribution between the measuring channel and the reference channel leads to a drift or deterioration of the measured signal. In addition, the measuring effect, i.e., the change in the signal quotient due to absorption, is frequently very small, so that it corresponds to a deviation of the signal quotient by 0.5%, e.g., in the case of a methane sensor based on the required accuracy of 1% of the lower explosion limit. However, such deviations of the signal quotient are likewise easily possible if, e.g., the beam splitter in the optical arrangement does not guarantee ideal splitting of the radiation between the active surfaces of the measuring radiation detector and the reference radiation detector, or if a shift in the image of the radiation source in the plane of the detectors is brought about by aging effects in the radiation source. If the beam spot moves over the edge of the active detector surface, the detector signal will change. A slight asymmetry in illumination thus produces an undesired deviation in the signal quotient. Similar deviations may also be caused by thermal deformations of the sensor structure or by dirt or liquid drops in the beam path, by mechanical shocks or other causes. As an end result, radiation components that are weighted unequally in the measuring and reference channels are thus blanked out.

Complicated technical measures are taken to avoid or reduce the above-described effects. For example, the housing and the carrying structure are made of high-quality metallic materials, and fits prepared with precision and true-to-angle mounts as well as adjustment steps are provided in the manufacturing process. Furthermore, structured intensity distributions in the effective detector surface are smoothened by blurred imaging or by a specific scattering of the radiation. The use of only one detector element with one movable filter wheel arranged in the beam path with different interference filters has been known as well.

SUMMARY AND OBJECTS OF THE INVENTION

The object of the present invention is to propose a simple design for an improved infrared optical gas sensor, which delivers more stable measured signals.

According to the invention an infrared optical gas sensor is provided with at least one infrared radiation source and with at least one infrared radiation detector. The infrared radiation detectors used as reference radiation and measuring radiation detectors are formed of thin layers of a partially transparent material, which delivers an electric measured signal that depends on the radiation intensity received. The infrared radiation detectors are stacked one over the other and are arranged with an intermediate narrow-band filter each, which transmits at the measuring wavelength. The infrared radiation detectors have an electrically conductive coating and are contacted on their top sides and undersides. The measuring radiation detector follows the reference radiation detector in the direction of the beam. The reference radiation detector is transparent for at least part of the measuring radiation at the measuring wavelength.

According to an alternative embodiment of the invention an infrared optical gas sensor is provided with at least one infrared radiation source and with at least one infrared radiation detector. The infrared radiation detectors used as reference radiation and measuring radiation detectors are formed of thin layers of a partially transparent material, which delivers an electric measured signal that depends on the radiation intensity received. The infrared radiation detectors are stacked one over the other and are arranged with an intermediate narrow-band filter each, which stop or block at the measuring wavelength. The infrared radiation detectors on the top side and the underside each have an electrically conductive coating and are contacted. The reference radiation detector follows the measuring radiation detector in the direction of the beam. The measuring radiation detector is transparent for at least part of the reference radiation at the reference wavelength.

One essential advantage of the present invention arises from the compact, layered design of a multiple detector arrangement for the measurement of at least two different wavelengths, namely, a reference wavelength and a measuring wavelength. In the simplest case, the gas sensor according to the present invention may be designed such that the measuring gas holder filled with the gas to be measured is an internally reflecting tube, which has a broad-band infrared radiation source at one end face and a layered multiple detector arrangement according to the present invention at the other, opposite end face. An infrared optical gas sensor with stable output signal is thus provided without an additional imaging optical system. The cylindrical reflector, i.e., the measuring gas holder, ensures increased radiation intensity in the central longitudinal axis of the measuring gas holder and thus also in the entry window of the multiple detector arrangement, which is mounted centrally in one end face of the measuring gas holder.

Contrary to the present invention, a double detector usually used hitherto with entry windows arranged next to one another has drawbacks in this regard due to reduced stability over time and geometric stability of the irradiated effective detector surfaces as well as due to the reduced radiation intensity received because of the impossibility of the geometrically identical arrangement of the two detectors in the central longitudinal axis of the sample holder. The multiple reflections on the cylindrical surface of the measuring gas holder lead to a radiation intensity distribution with a maximum in the central longitudinal axis and a steep drop in intensity in the radial direction. The radiation-sensitive detector surfaces are thus located on the flanks of this intensity distribution, so that the measured radiation intensity strongly depends on the position of the infrared radiation detectors and the change in this position.

The measuring and reference radiation detectors are designed as a thin, partially transparent layer. This may be a thin, plane-parallel disk or layer of a pyroelectric material, which has a preferably transparent, electrically conductive coating on the top side and the underside and is contacted. Suitable pyroelectric materials include especially the crystalline substances lithium tantalate ($LiTaO_3$), strontium barium niobate (SBN), triglycine sulfate (TGS), lead zirconium titanate (PZT), and the polyvinylidene fluoride (PVDF) polymer. It is also possible to use semiconductors, which utilize the inner photo effect for the radiation detection, which is possible in the case of HgCdTe, PbS and PbSe. The design of the detector elements and the contacting must permit the passage of the radiation without shadowing. Transparent conductive layers are especially metallic layers with thicknesses in the range of a few nm or transparent layers such as ITO (indium tin oxide).

A narrow-band filter, which further narrows the spectral component of the incident radiation, is arranged between two layers. A narrow-band filter, which lets through the spectral range containing the measuring and reference wavelengths, may be likewise arranged in front of the first radiation-sensitive layer. The transmission ranges of the filters must be selected to be such that they overlap in at least one partial range. The thickness of the first radiation-sensitive layer must be selected to be such that a sufficient component of the radiation will be both absorbed and transmitted. Layer thicknesses of 20 to 30 $\mu$m can be obtained by polishing crystalline materials such as lithium tantalate ($LiTaO_3$). Films made of polyvinylidene fluoride (PVDF) of a comparable layer thickness belong to the state of the art. Layer thicknesses beginning from 1 $\mu$m have been obtained for triglycine sulfate (TGS).

The absorption of radiation in the transparent layer is enhanced by a narrow-band filter, which follows in the beam path and is preferably designed as an interference filter, reflecting the component of the radiation that it does not transmit. This component will again pass through the first detector layer and can be absorbed. If the structure comprises more than two partial detectors, this also applies to the succeeding partial detectors.

In the case of the polymer layer consisting of polyvinylidene fluoride (PVDF), a natural selective absorption is present in the range of 3.3 $\mu$m, which can be further increased by adding hydrocarbon monomers. With this layer as the first layer in the path of the light, hydrocarbons can be measured selectively without a corresponding narrow band filter having to be arranged in front of it. At the same time, this layer filters out the component of the incident spectrum that is absorbed by hydrocarbons in the atmosphere. As a result, the succeeding detector layer receives the radiation component that is extensively independent from changes in the concentrations of hydrocarbons in the path of the light. This results in a special embodiment of the subject of the present invention.

The last detector layer in the detector structure permits a greater freedom of design. In the case of pyroelectric layers, the entry surface may be blackened in order to achieve complete absorption of the residual radiation. The electrodes do not have to be transparent here. A more complete semiconductor detector with pn transition and electrode structures applied to the reverse side may be used as well.

The strong effect of the thermal environment on the signal must be borne in mind in the case of the use of pyroelectric crystals for the individual detector layers. Direct contact of the crystal or film with a narrow-band filter leads to a markedly changed behavior with respect to an unsupported layer especially in the range of low radiation modulation frequencies. The intermediate space must be designed here with respect to the heat conduction from the pyroelectric crystal to the environment such that the sensitivity of the layer becomes optimal. This is achieved by means of suitable substrate materials with low heat capacity and thermal conductivity or by means of an air gap. The thickness of the intermediate space is about 0.3 to 1 mm. The entire layer structure may be accommodated in a usual standard housing, whose entry opening is a diaphragm for the entering radiation. The topmost layer of the structure may be used as an entry window, and this layer may be bonded or soldered to the housing to achieve gas tightness. The diaphragm ensures, among other things, that each entering light beam must travel through all layers of the structure. It is thus ruled out that a component of the radiation reaches only one of the partial detectors and thus leads to a drift of the signal quotient in the case of a change.

To compensate the effect of changing ambient temperatures, one or more additional pyroelectric elements may be added, whose signals are used for negative feedback. To eliminate a sensitivity to the incident radiation, such elements are preferably provided with a gold surface.

For a double detector for measuring $CO_2$, the transmission window for the narrow-band filter in the radiation entry (reference filter) may cover the range of 4.0 to 4.4 $\mu$m. The next filter (measuring filter) will then cover the absorption band of $CO_2$ around 4.24 $\mu$m with a width of 100 to 200 nm. As an alternative, both transmission ranges may be selected such that they overlap only in the range of the absorption band of $CO_2$, but the reference filter must contain an additional range, in which $CO_2$ does not absorb.

The layer thickness of the infrared radiation detectors according to the present invention is about 1 to 30 $\mu$m, and the layer thickness of the narrow-band filters is about 0.3 to 1 mm.

Depending on the particular embodiment of the present invention, the narrow-band filters according to the invention are preferably designed either as interference filters with a narrow transmission range or as interference filters with a narrow stop band or as absorption filters with narrow absorption range. For example, the one narrow-band filter or the plurality of narrow-band filters according to one embodiment is/are preferably an interference filter/interference filters with a narrow transmission range, so that ideally only measuring radiation with the gas-specific wavelength will reach the next layer forming the measuring radiation detector. The other two embodiments of narrow-band filters mentioned are correspondingly suitable preferably for other variants of the present invention.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
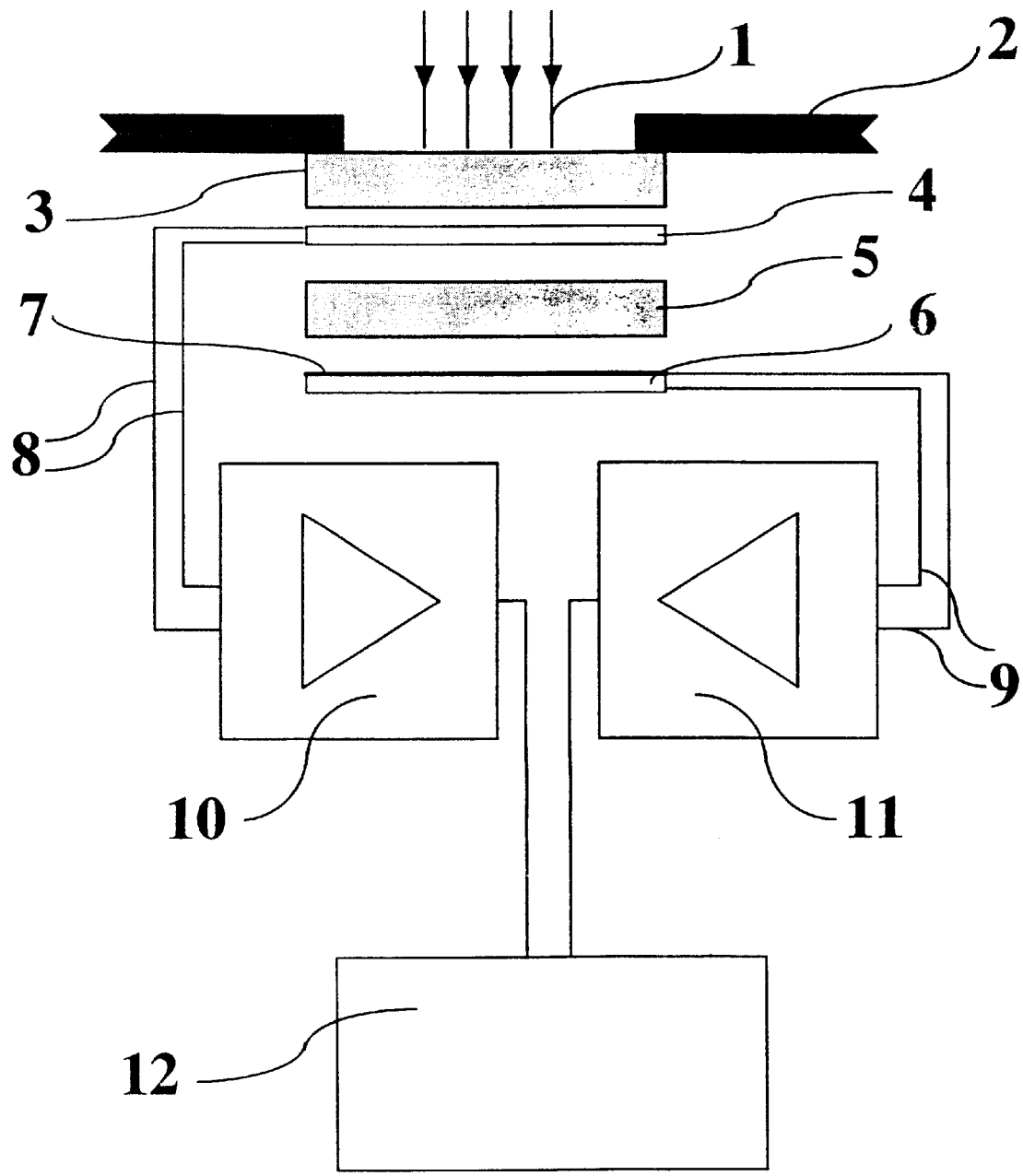
FIG. 1 is a schematic view showing a layered detector arrangement of an infrared optical gas sensor according to the present invention.

Referring to the drawings in particular, FIG. 1 shows a detector arrangement which is located centrally symmetrically to the central longitudinal axis of the radiation (arrows) of an infrared radiation source 21 entering through the entry opening 1 (arrows), after passing through the gas to be measured, whose concentration is to be determined.

The detector arrangement comprises a plurality of parallel layers, which are built in a housing 2 of a gas holder 22.

In the exemplary embodiment of FIG. 1, a thin-layer pyroelectric reference radiation detector 4 with an upstream narrow-band filter 3 as well as a subjacent measuring radiation detector 6 with an interposed narrow-band filter 5 are arranged stacked. The measuring radiation detector 6 in this example consists of a pyroelectric material and is blackened with an absorption layer 7 in the radiation entry area in order to achieve complete absorption of the entering radiation. The electric output signals of the detector layers are sent by means of the contact lines 8 and 9 to the amplifiers 10 and 11, whose output signals are in turn evaluated in a prior-art electronic evaluation unit 12 by forming the quotient of the reference and measured signals, and they are finally outputted and displayed as concentration values of the measured gas.

Figure 2:
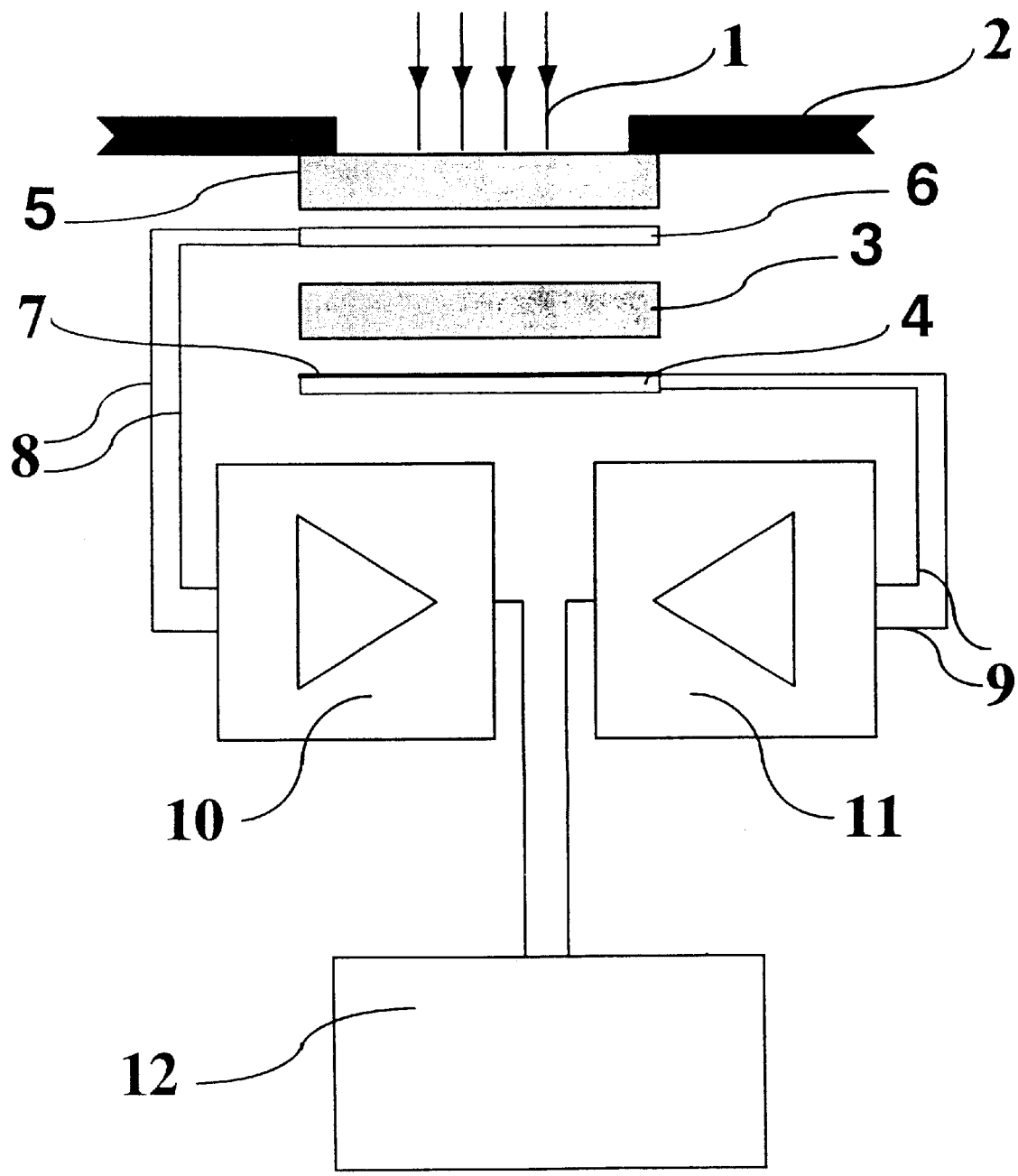
FIG. 2 is a schematic view showing a layered detector arrangement of an infrared optical gas sensor according to another embodiment of the present invention.
Figure 3:
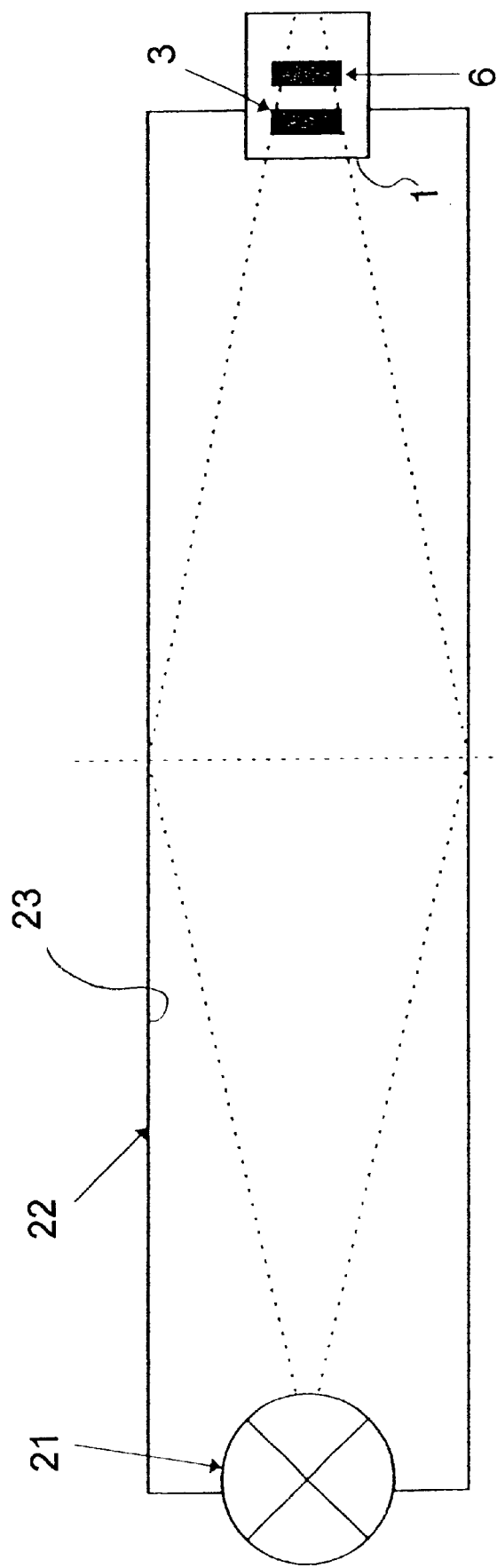
FIG. 3 is a schematic view of the gas holder, the radiation source and the detectors.

In the exemplary embodiment of FIG. 2, a thin-layer pyroelectric measuring radiation detector 6 with an upstream narrow-band filter 5 as well as a subjacent reference radiation detector 4 with an interposed narrow-band filter 3 are arranged stacked. The reference radiation detector 4 in this example of FIG. 2 is formed of a pyroelectric material and is blackened with an absorption layer 7 in the radiation entry area in order to achieve complete absorption of the entering radiation. The electric output signals of the detector layers are sent by means of the contact lines 8 and 9 to the amplifiers 10 and 11, whose output signals are in turn evaluated in a prior-art electronic evaluation unit 12 by forming the quotient of the reference and measured signals, and they are finally outputted and displayed as concentration values of the measured gas.

The measuring and reference radiation detectors 6, 4 are designed as a thin, partially transparent layer. This is a thin, plane-parallel disk or layer of a pyroelectric material, which has a transparent, electrically conductive coating on the top side and the underside and is contacted. The device of the FIGURES may be provided with pyroelectric materials including especially the crystalline substances lithium tantalate ($LiTaO_3$), strontium barium niobate (SBN), triglycine sulfate (TGS), lead zirconium titanate (PZT), and the polyvinylidene fluoride (PVDF) polymer. It is also possible to use semiconductors, which utilize the inner photo effect for the radiation detection, which is possible in the case of HgCdTe, PbS and PbSe. The design of the detector elements 4 and 6 permits the passage of the radiation without shadowing. The transparent conductive layers are metallic layers with thicknesses in the range of a few nm or transparent layers such as ITO (indium tin oxide).

The narrow-band filter 5, which further narrows the spectral component of the incident radiation, is arranged between two layers. The narrow-band filter 3, which lets through the spectral range containing the measuring and reference wavelengths, may be likewise arranged in front of the first radiation-sensitive layer. The transmission ranges of the filters 5, 3 must be selected to be such that they overlap in at least one partial range. The thickness of the first radiation-sensitive layer must be selected to be such that a sufficient component of the radiation will be both absorbed and transmitted. Layer thicknesses of 20 to 30 $\mu$m are obtained by polishing crystalline materials such as lithium tantalate ($LiTaO_3$). Films made of polyvinylidene fluoride (PVDF) of a comparable layer thickness are themselves known. Layer thicknesses beginning from 1 $\mu$m have been obtained for triglycine sulfate (TGS).

The absorption of radiation in the transparent layer is enhanced by a narrow-band filter, which follows in the beam path and is preferably designed as an interference filter, reflecting the component of the radiation that it does not transmit. This component will again pass through the first detector layer and can be absorbed. If the structure comprises more than two partial detectors, this also applies to the succeeding partial detectors.

In the case of the polymer layer consisting of polyvinylidene fluoride (PVDF), a natural selective absorption is present in the range of 3.3 $\mu$m, which can be further increased by adding hydrocarbon monomers. With this layer as the first layer in the path of the light, hydrocarbons can be measured selectively without a corresponding narrow band filter having to be arranged in front of it. At the same time, this layer filters out the component of the incident spectrum that is absorbed by hydrocarbons in the atmosphere. As a result, the succeeding detector layer receives the radiation component that is extensively independent from changes in the concentrations of hydrocarbons in the path of the light. This results in a special embodiment of the subject of the present invention.

The last detector layer in the detector structure permits a greater freedom of design. In the case of pyroelectric layers, the entry surface may be blackened in order to achieve complete absorption of the residual radiation. The electrodes do not have to be transparent here. A more complete semiconductor detector with pn transition and electrode structures applied to the reverse side may be used as well.

The strong effect of the thermal environment on the signal must be borne in mind in the case of the use of pyroelectric crystals for the individual detector layers. Direct contact of the crystal or film with a narrow-band filter leads to a markedly changed behavior with respect to an unsupported layer especially in the range of low radiation modulation frequencies. The intermediate space must be designed here with respect to the heat conduction from the pyroelectric crystal to the environment such that the sensitivity of the layer becomes optimal. This is achieved by means of suitable substrate materials with low heat capacity and thermal conductivity or by means of an air gap. The thickness of the intermediate space is about 0.3 to 1 mm. The entire layer structure may be accommodated in a usual standard housing, whose entry opening is a diaphragm for the entering radiation. The topmost layer of the structure may be used as an entry window, and this layer may be bonded or soldered to the housing to achieve gas tightness. The diaphragm ensures, among other things, that each entering light beam must travel through all layers of the structure. It is thus ruled out that a component of the radiation reaches only one of the partial detectors and thus leads to a drift of the signal quotient in the case of a change.

To compensate the effect of changing ambient temperatures, one or more additional pyroelectric elements may be added, whose signals are used for negative feedback. To eliminate a sensitivity to the incident radiation, such elements are provided with a gold surface.

For a double detector for measuring $CO_2$, the transmission window for the narrow-band filter in the radiation entry (reference filter) may cover the range of 4.0 to 4.4 $\mu$m. The next filter (measuring filter) will then cover the absorption band of $CO_2$ around 4.24 $\mu$m with a width of 100 to 200 nm. As an alternative, both transmission ranges may be selected such that they overlap only in the range of the absorption band of $CO_2$, but the reference filter must contain an additional range, in which $CO_2$ does not absorb.

The layer thickness of the infrared radiation detectors according to the present invention is about 1 to 30 $\mu$m, and the layer thickness of the narrow-band filters is about 0.3 to 1 mm.

Depending on the particular embodiment of the present invention, the narrow-band filters are designed either as interference filters with a narrow transmission range or as interference filters with a narrow stop band or as absorption filters with narrow absorption range. For example, the one narrow-band filter or the plurality of narrow-band filters according to one embodiment is/are an interference filter/interference filters with a narrow transmission range, so that ideally only measuring radiation with the gas-specific wavelength will reach the next layer forming the measuring radiation detector. The other two embodiments of narrow-band filters mentioned are correspondingly suitable for other variants of the present invention.

The gas sensor according to the present invention may be designed such that the measuring gas holder 22 filled with the gas to be measured is an internally reflecting tube, which has a broad-band infrared radiation source 21 at one end face and a layered multiple detector arrangement 3–7 according to the present invention at the other, opposite end face. A cylindrical reflector 23 is part of the inside of the measuring gas holder 22 and ensures increased radiation intensity in the central longitudinal axis of the measuring gas holder and thus also in the entry window 1 of the multiple detector arrangement, which is mounted centrally in one end face of the measuring gas holder 22.

While specific embodiments of the invention have been shown and described in detail to illustrate the application of the principles of the invention, it will be understood that the invention may be embodied otherwise without departing from such principles.

What is claimed is:
1. An infrared optical gas sensor comprising:
   a first pyroelectric radiation detector receivable of first and second types of radiation, and generating a first electrical signal proportional to an intensity of the first type of radiation received, said first radiation detector being transparent to the second type of radiation;
   a second pyroelectric radiation detector arranged downstream of said first radiation detector in a direction of the radiation and receivable of the second type of radiation from said first detector, said second detector generating a second electrical signal proportional to an intensity of the second type of radiation received, said first pyroelectric radiation detector and said second pyroelectric radiation detector being stacked one over the other with said second radiation detector following said first radiation detector in the direction of the radiation.
2. A sensor in accordance with claim 1, wherein:
   a material and a thickness of said first detector is selected to cause said first detector to be transparent to the second type of radiation.
3. A sensor in accordance with claim 2, wherein:
   said second detector is formed of substantially the same material as, and of substantially the same thickness as, said first detector, said second detector includes a layer substantially completely absorbing of the radiation from said first detector.
4. A sensor in accordance with claim 1, further comprising:
   a gas holder including an internally reflecting tube, said radiation detectors being positioned at one end of said tube;
   a radiation source positioned at another end of said tube to pass radiation through said tube, said tube forming a cylindrical reflector for said radiation source to increase radiation intensity in a central longitudinal axis of said tube.
5. A sensor in accordance with claim 1, further comprising:
   a first radiation type filter to block said first type of radiation, said first radiation type filter being arranged between said first and second radiation detectors.
6. A sensor in accordance with claim 5, wherein:
   said second radiation detector is spaced from said first radiation type band filter by one of an air gap or by a partially transparent substrate material of low thermal conductivity.
7. A sensor in accordance with claim 5, wherein:
   said first radiation type band filter is an interference filter.
8. A sensor in accordance with claim 5, wherein:
   said filter is an absorption filter.
9. A sensor in accordance with claim 1, wherein:
   said radiation detector includes one of the substances lithium tantalate ($LiTaO_3$), strontium barium niobate (SBN), triglycine sulfate (TGS), lead zirconium titanate (PZT), and polyvinylidene fluoride (PVDF).
10. A sensor in accordance with claim 1, further comprising:
    a first and second radiation type band filter which is transparent to said first and second types of radiation, and is arranged upstream of said first radiation detector.
11. A sensor in accordance with claim 10, wherein:
    said filter is an interference filter.

12. A sensor in accordance with claim 10, wherein:
said filter is an absorption filter.

13. A sensor in accordance with claim 1, wherein:
a thickness of said first radiation detector is approximately 1 to 30 μm.

14. A sensor in accordance with claim 1, wherein:
said second radiation detector has a radiation entry surface with a radiation absorption layer.

15. A sensor in accordance with claim 1, wherein:
one of said radiation detectors is combined with a narrow-band filter, the combination including a pyroelectric polymer with a natural selective infrared absorption.

16. A sensor in accordance with claim 15, wherein:
said pyroelectric polymer with a natural selective infrared absorption is polyvinylidene fluoride (PVDF).

17. A sensor in accordance with claim 16, wherein:
said polyvinylidene fluoride (PVDF) has monomeric hydrocarbons added.

18. A sensor in accordance with claim 1, wherein:
said first radiation detector is combined with a downstream narrow-band filter, said combination forming a layer including polyvinylidene fluoride (PVDF).

19. A sensor in accordance with claim 1, wherein:
a thickness of said infrared radiation detectors is approximately 1 to 30 μm.

20. A sensor in accordance with claim 1, further comprising:
an electrically conductive coating disposed on said first and second radiation detectors, and electrically contacted on a top side and an underside of said first and second radiation detectors.

* * * * *